United States Patent [19]

Reilly, Jr.

[11] Patent Number: 4,503,223
[45] Date of Patent: Mar. 5, 1985

[54] PROCESS FOR THE PURIFICATION OF N-MORPHOLINOALKYL DIHYDROPYRIDINES

[75] Inventor: Laurence W. Reilly, Jr., Yorktown Heights, N.Y.

[73] Assignee: USV Pharmaceutical Corporation, Tarrytown, N.Y.

[21] Appl. No.: 522,299

[22] Filed: Aug. 11, 1983

[51] Int. Cl.$^3$ ............................................. C07D 413/06
[52] U.S. Cl. ..................................... 544/122; 544/128; 544/131
[58] Field of Search ........................ 544/122, 128, 131

[56] References Cited

U.S. PATENT DOCUMENTS 4,258,042  3/1981  Loev et al. ...................... 549/131

Primary Examiner—Robert W. Ramsuer

[57] ABSTRACT

N-Morpholinoalkyl dihydropyridines are purified by precipitating their acid addition salts in an acidic organic solvent, dissolving the precipitate in a two-phase solvent system and crystallizing the N-morpholinoalkyl dihydropyridines from the organic phase of the two-phase solvent system.

23 Claims, No Drawings

PROCESS FOR THE PURIFICATION OF N-MORPHOLINOALKYL DIHYDROPYRIDINES

BACKGROUND OF THE INVENTION

1. Field of the Invention

This invention relates to the purification of N-morpholinoalkyl dihydropyridines.

2. Description of the Prior Art

U.S. Pat. No. 4,258,042 describes and claims N-morpholinoalkyl dihydropyridines of the formula

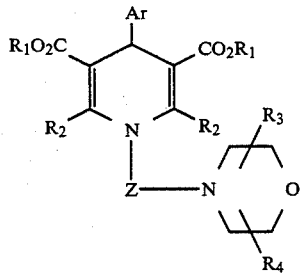

wherein Ar is heteroaryl, cycloalkyl having from 3 to 7 carbon atoms, naphthyl, indanyl, indenyl, tetrahydronaphthyl or a radical of formula

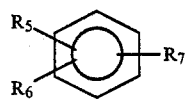

wherein each of $R_5$, $R_6$ and $R_7$ is independently H, alkyl, aryl, halo, lower alkoxy, nitro, alkylmercapto, cyano, carboxy, carbalkoxy, sulfamyl, trifluoromethyl, hydroxy, acyloxy, methanesulfonyl, or acylamino; and $R_5$ and $R_6$ when taken together form a methylenedioxy; Z is alkylene containing 1 to about 5 carbon atoms in the principal chain, and each $R_1$ is independently hydrogen, alkyl, or alkoxyalkyl, with the proviso that only one $R_1$ may be hydrogen; $R_2$ is lower alkyl; $R_3$ and $R_4$ are independently hydrogen or lower alkyl. The total number of carbon atoms in each of the alkyl, acyl, and alkoxy groups can range up to about 10, and preferably contain up to 6 carbon atoms. The substituent "Z" contains up to about 5 carbons in the principal chain, i.e. the straight chain of carbons between the terminal valences, but can be branched in that methyl and ethyl substituents can be present on the principal chain. Thus, the alkylene chain Z can contain a total number of carbon atoms greater than 5, preferably no more than about 8.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene and substituted heterocycles.

N-morpholinoalkyl dihydropyridines can be prepared, as stated in the patent, by art-recognized procedures from known starting materials. A particularly convenient preparative method utilizes the following:

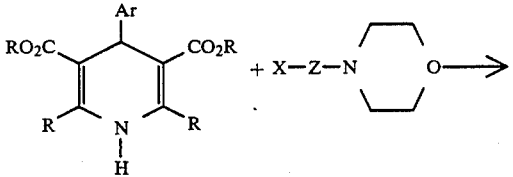

The reaction can be carried out in a solvent in the presence of sodium hydride, or any alkali metal hydride or alkoxide as is commonly employed in condensation reactions. The reaction is effected in two steps, the first metallation with the alkali metal compound, and the second, condensation with the halide, "X", containing compound, which is usually chloride. The hydrides are convenient since the progress of the metallation reaction can be followed by observing the evolution of hydrogen gas. The metallation step is normally carried out at room temperature. The reaction mixture thereafter is heated at elevated temperature, e.g. at steam bath temperature at or about 100° C. depending on the boiling point of the selected solvent, and the halide compound is then added, usually in controlled amounts in dropwise fashion and, after addition is completed, the reaction mixture is digested by heating at the elevated temperature.

The product is then obtained in the usual fashion, as by cooling to cause precipitation or evaporation of the solvent to obtain the product as a residue.

The compounds so obtained possess high antihypertensive activity and as such are of particular value as antihypertensive agents. However, it has been observed that the use of the above-described method of preparation results in the production of N-morpholinoalkyl dihydropyridines that contain a small and varying amount of the starting material.

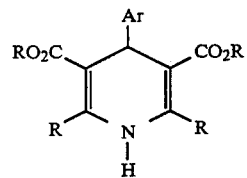

This residual impurity which at times may be 0.5% or more is undesirable in compounds designed for clinical applications where essential requirements such as proper dose, potency, high purity and absence of side effects must be strictly met. While residual amounts of the starting material could be further reduced via classical means of purification such as chromatography, multiple recrystallization and the like, such means are cumbersome, impractical and costly, on a large scale.

Accordingly, it is the principal object of the present invention to provide a method of purification for N-morpholinoalkyl dihydropyridines.

It is a further object of the present invention to provide a large scale method of purification for N-morpholinoalkyl dihydropyridines.

It is another object of the present invention to provide a large scale, simple and economical method of purification for N-morpholinoalkyl dihydropyridines.

It is still another object of the present invention to produce N-morpholinoalkyl dihydropyridines that are essentially free of the residual starting material.

SUMMARY OF THE INVENTION

The objects of the present invention are accomplished in a process of purification which comprises:

(a) dissolving the crude N-morpholionalkyl dihydropyridine in an organic solvent (solution A);

(b) dissolving an organic acid in an organic solvent to obtain an acid solution (solution B);

(c) adding with mixing solution B to solution A to precipitate the acid addition salt of N-morpholinoalkyl dihydropyridine;

(d) collecting the acid addition salt precipitate;

(e) dissolving the collected acid addition salt in a two-phase solvent, one of said two-phase solvent being an alkaline aqueous phase and the other a water immisible organic phase;

(f) separating the water immiscible organic phase from the aqueous phase; and (g) crystallizing the purified N-morpholinoalkyl dihydropyridine from said water immiscible organic phase with a organic solvent.

The products made by the purification process of the present invention are essentially free of any residual starting material.

DETAILED DESCRIPTION OF THE INVENTION

The present invention is now described in more detail with reference to the purification steps described hereinbefore.

(a) The present invention utilizes as starting material the crude N-morpholinoalkyl dihydropyridines having the formula

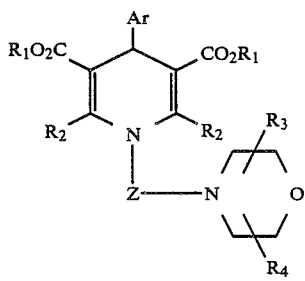

wherein:

Ar is heteroaryl, cycloalkyl having from 3 to 7 carbon atoms, naphthyl, indanyl, indenyl, tetrahydronaphthyl or a radical of formula

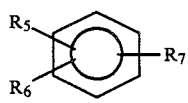

wherein each of $R_5$, $R_6$ and $R_7$ is independently H, alkyl, aryl, halo, lower alkoxy, nitro, alkylmercapto, cyano, carboxy, carbalkoxy, sulfamyl, trifluoromethyl, hydroxy, acyloxy, methanesulfonyl, or acylamino; and $R_5$ and $R_6$ when taken together form a methylenedioxy;

Z is alkylene containing 1 to about 5 carbon atoms in the principal chain; and each $R_1$ is independently hydrogen, alkyl, or alkoxyalkyl, with the proviso that only one $R_1$ may be hydrogen;

$R_2$ is lower alkyl;

$R_3$ and $R_4$ are independently hydrogen or lower alkyl.

The total number of carbon atoms in each of the alkyl, acyl, and alkoxy groups can range up to about 10, and preferably contain up to 6 carbon atoms. The substituent "Z" contains up to about 5 carbons in the principal chain, i.e. the straight chain of carbons between the terminal valences, but can be branched in that methyl and ethyl substituents can be present on the principal chain. Thus, the alkylene chain Z can contain a total number of carbon atoms greater than 5, preferably no more than about 8.

Heteroaryl as employed herein refers to any heterocyclic structure in which at least one of O, S and N are present as the hetero atoms. These include thiophene, furan, pyridine, thiazole, pyrimidine, pyrrole, benzofuran, quinoline, benzothiophene and substituted heterocycles.

Compounds of this formula are about 95% pure and may contain as much as 0.3 to about 5% of

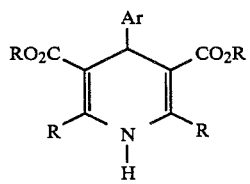

A compound of this formula is dissolved in an organic solvent to obtain a solution of 1 to 50% w/v and preferably 5 to 25% w/v thereof. The organic solvent can be any solvent that is capable of dissolving the compound, examples of which are ethyl acetate, toluene, methylene chloride, tetrahydrofuran, diethyl ether, acetonitrile, carbon tetrachloride, chloroform, dioxane and acetone. The preferred solvents are ethyl acetate and toluene.

Alternatively, the crude N-morpholinoalkyl dihydropyridines can be prepared from the reaction mixture

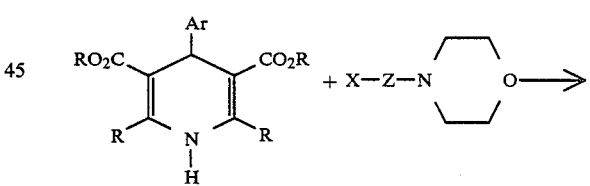

(as described in U.S. Pat. No. 4,258,042) by workup of this reaction mixture as will be described in the examples that follow.

(b) Another solution is prepared, for use with the solution prepared in step (a), by dissolving an acid in an organic solvent to obtain a solution thereof having a concentration of 1 to 50% w/v and preferably 5 to 25% w/v. The acid used is preferably an organic acid which can be solubilized in the organic solvent of choice, such as maleic, tartaric, acetic, glycolic, succinic, nicotinic, arylsulfonic, e.g., p-toluenesulfonic, fumaric, methanesulfonic and pamoic acids. The preferred acids are p-toluenesulfonic and maleic acids.

Alternatively, mineral acids that are compatible with the organic solvent used in step (a) may also be used, such as hydrochloric, hydroiodic, hydrobromic, phosphoric, metaphosphoric, nitric or sulfuric acids dissolved, e.g., in water or 2-propanol. The organic solvent may be any of the organic solvents described in (a) or mixtures thereof.

(c) The organic acid solution is added to the solution of the crude compound while the same being mixed, stirred or agitated so as to precipitate the acid addition salt of the N-morpholinoalkyl dihydropyridines of the formula

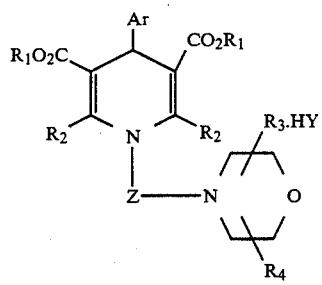

wherein Y is the particular conjugate base of the acid used in step (b), namely, maleic, tartaric, acetic, glycolic, succinic, nicotinic, p-toluenesulfonic, fumaric, methanesulfonic or pamoic.

(d) The precipitate obtained in (c) is collected by known methods used in the art, such as by filtration or centrifugation.

(e) The precipitate is dissolved in a two-phase solvent system, one being an alkaline aqueous phase and the other being a water immiscible organic phase. The alkaline aqueous phase of the two-phase solvent system is prepared by dissolving a base, e.g., NaOH, KOH, $NA_2CO_3$, $NaHCO_3$, $K_2CO_3$, $KHCO_3$, $NH_4OH$, LiOH, $Li_2CO_3$, $LiHCO_3$ and the like in water so that a solution of 1 to 50% w/v and preferably 5 to 25% w/v is obtained. The water immiscible phase of the two-phase solvent system consist of a water immiscible organic solvent, such as ethyl acetate, toluene, methylene chloride, diethyl ether, carbon tetrachloride or chloroform. The preferred water immiscible organic solvent is toluene. The ratio of the aqueous alkaline phase to the water immiscible organic phase of the two-phase solvent system should be in the range of 1:5 to 10:1 and preferably in the range of 1:2 to 5:1. The dissolving of the precipitate is accomplished by agitation, such as stirring and mixing.

(f) Upon completing dissolution of the precipitate in the two-phase solvent system, the aqueous alkaline phase is separated from the water immiscible phase by a conventional technique, such as decantation or drawing off one phase via a separatory funnel.

(g) The desired end product is then purified via crystallization by diluting the water immiscible organic phase with an organic solvent in a ratio of 3:1 to 1:10 and preferably 2:1 to 1:5. The organic solvent used for this dilution may be heptane, n-hexane, hexanes, 2-methylhexane, 3-methylhexane, 2,2-dimethylpentane, 2,3-dimethylpentane, 3,3-dimethylpentane, cyclohexane, methylcyclohexane, isooctane, 2-methylpentane, 3-methylpentane, 2-propanol, methanol, ethanol and the like. Preferably, the organic solvent used in the crystallization of the desired end product is heptane, n-hexane or hexanes.

The purified end product obtained by the process of the present invention is about >99.5% pure and contains about 0.01 to 0.30% of the starting material

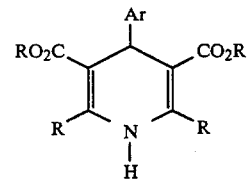

The following examples further illustrate the invention.

EXAMPLE 1

Diethyl 1,4-dihydro-2,6-dimethyl-1-[2-(4-morpholinyl)ethyl]-4-[2-(trifluoromethyl)phenyl]-3,5-pyridinedicarboxylate A suspension of 30.3 g (0.758 mol) of 60% NaH in mineral oil in 164 ml of DMF was cooled to 3° C. and a solution of 100.0 g (0.252 mol) of diethyl 1,4-dihydro-2,6-dimethyl-4-[2-(trifluoromethyl)phenyl]3,5-pyridinedicarboxylate in 100 ml of warm DMF was added dropwise over 30 min, keeping the temperature at 15° C. or less. After the addition was complete, 75.5 g (0.406 mol) of N-(2-chloroethyl)morpholine hydrochloride was added in portions over 25 min, keeping the temperature at approximately 15° C. The cooling bath was then replaced with a heating mantle and the reaction mixture was heated at 84°–100° C.for 4.5 hrs. After cooling to 31° C. over 50 min, the reaction mixture was poured into a stirred mixture of 500 ml of $H_2O$ and 300 ml of EtOAc. When all the solids dissolved, the phases were separated and the EtOAc phase was dried over anhydrous $Na_2SO_4$ and filtered. To this stirred EtOAc solution was added a solution of 47.9 g (0.252 mol) of p-TSA $H_2O$ in 300 ml of EtOAc, giving immediate precipitation of diethyl 1,4-dihydro-2,6-dimethyl-1-[2-(4-morpholinyl)-ethyl]-4-[2-(trifluoromethyl)-phenyl]-3,5-pyridinecarboxylate p-toluenesulfonate salt. After stirring for 20 min, the product was collected, washed with EtOAc, and dried in vacuo to yield 114.5 g (67%) of diethyl 1,4-dihydro-2,6-dimethyl-1-[2-(4-morpholinyl)ethyl]-4-[2-(trifluoromethyl)-phenyl]-3,5-pyridinedicarboxylate p-toluenesulfonate salt as a white solid: mp 204°–206° C. (dec.).

Anal. calcd. for $C_{33}H_{41}N_2O_8S$: C, 58.05; H, 6.05; N, 4.10. Found: C, 57.66; H, 6.02; N, 3.69.

The compound obtained above (109.7 g; 0.161 mol) was partitioned between 275 ml of toluene and 550 ml of 10% NaOH. The toluene phase was dried over anhydrous $Na_2SO_4$, filtered, and treated with 550 ml of heptane. The solution was stirred for 1 hr, during which time a considerable amount of diethyl 1,4-dihydro-2,6-dimethyl-1-[2-(4morpholinyl)ethyl]-4-[2-(trifluoromethyl)phenyl]-3,5-pyridinedicarboxylate had crystallized. The solution was cooled to −15° C. for 4 hrs. and the precipitate was collected, washed with heptane, and dried in vacuo to yield 70.7 g (86%) of diethyl 1,4-dihydro-2,6-dimethyl-1-[2-(4-morpholinyl)ethyl]-4-[2-(trifluoromethyl)phenyl]-3,5-pyridinedicarboxylate. Analysis by analytical HPLC showed diethyl 1,4-dihydro-2,6-dimethyl-4-[2-(trifluoromethyl)phenyl]-3,5-pyridinedicarboxylate to be present at a level of 0.02%.

EXAMPLE 2

Diethyl 1,4-dihydro-2,6-dimethyl-1-[2-(4-morpholinyl)ethyl]-4-[2-(trifluoromethyl)phenyl]-3,5-pyridinedicarboxylate A solution of 1.2 g (0.010 mol) of maleic acid in 6 ml of acetone was poured into a solution of 5.1 g (0.010 mole) of diethyl 1,4-dihydro-2,6-dimethyl-1-[2-(4-morpholinyl)ethyl]-4-[2-(trifluoromethyl)phenyl]-3,5-pyridinedicarboxylate in 30 ml of toluene. The precipitated solid was collected, washed with toluene, and dried to yield 6.1 g (97%) of 1,4-dihydro-2,6-dimethyl-1-[2-(4-morpholinyl)ethyl]-4-[2-(trifluoromethyl)phenyl]-3,5-pyridinedicarboxylate maleate. This material was partitioned between 30 ml of toluene and 25 ml of 10% aqueous NaOH and the separated toluene phase was diluted with 60 ml of heptane. Chilling overnight yielded 3.4 g (67%) of diethyl 1,4-dihydro-2,6-dimethyl-1-[2-(4-morpholinyl)ethyl[4-[2-(trifluoromethyl)phenyl]-3,5-pyridinedicarboxylate. Recrystallization from 10 ml of 2-propanol yielded 2.9 g of the title compound which contained, as determined by HPLC, 0.19% of

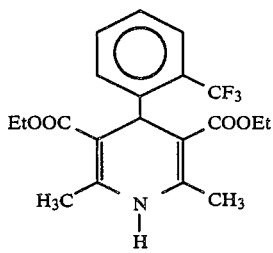

EXAMPLE 3

Diethyl 1,4-dihydro-2,6-dimethyl-1-[2-(4-morpholinyl)ethyl]-4-[2-(trifluoromethyl)phenyl]-3,5-pyridinedicarboxylate A solution of 1.2 g of maleic acid in 12 ml of acetone was added to a solution of 5.1 g of diethyl 1,4-dihydro-2,6-dimethyl-1-[2-(4-morpholinyl)ethyl]-4-[2-(trifluoromethyl)phenyl]-3,5-pyridinedicarboxylate in 50 ml of EtOAc. The reaction mixture was refluxed and filtered hot to yield 6.7 g of diethyl 1,4-dihydro-2,6-dimethyl-1-[2-(4-morpholinyl)ethyl]-4-[2-(trifluoromethyl)phenyl]-3,5-pyridinedicarboxylate maleate. This was partitioned between 5 parts of toluene and 10 parts of 10% NaOH, the toluene phase was dried over anhydrous Na₂SO₄, and dilution with 10 parts of heptane yielded 3.9 g (76%) of diethyl 1,4-dihydro-2,6-dimethyl-1-[2-(4-morpholinyl)ethyl]-4-[2-(trifluoromethyl)phenyl]-3,5-pyridinecarboxylate. Analysis by analytical HPLC indicated the presence of 0.17% of

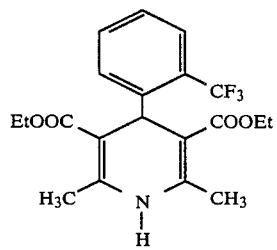

EXAMPLE 4

Diethyl 1,4-dihydro-2,6-dimethyl-1-[2-(4-morpholinyl)ethyl]-4-[2-(trifluoromethyl)phenyl]-3,5-pyridinedicarboxylate The procedure of Example 3 was repeated using 1.9 g of p-toluenesulfonic acid in 19 ml of EtOAc in place of maleic acid/acetone. A total of 3.6 g (71%) of the title compound was obtained containing 0.03% of the residual compound shown in Example 3 (as determined by analytical HPLC).

While the present invention has been illustrated with certain specific examples, it will be readily apparent to those skilled in the art that the invention is not limited thereto, and that various changes and modifications may be made without departing from the spirit of the invention or the scope of the appended claims.

What is claimed is:

1. A process for the purification of a compound of the formula

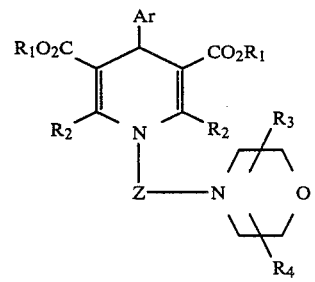

wherein Ar is heteroaryl, cycloalkyl having from 3 to 7 carbon atoms, naphthyl, indanyl, indenyl, tetrahydronaphthyl, or a radical of the formula

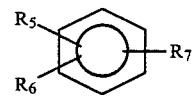

wherein each of $R_5$, $R_6$ and $R_7$ is independently H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino, and $R_5$ and $R_6$ when taken together, form a methylenedioxy; Z is alkylene containing 1 to about 5 carbon atoms in the principal chain; each $R_1$ is independently hydrogen, alkyl or alkoxyalkyl, with the proviso that only one $R_1$ may be hydrogen; $R_2$ is lower alkyl and $R_3$ and $R_4$ are independently hydrogen or alkyl; wherein the alkyl, alkoxy, and acyl groups contain up to 10 carbon atoms;

comprising the steps of:
dissolving said compound in an organic solvent;
precipitating an acid addition salt of said compound by adding a solution of an acid in an organic solvent thereto;
collecting said precipitate;
dissolving said precipitate in a two-phase solvent, one of said two-phase solvent being an alkaline aqueous phase and the other a water immiscible organic phase;
separating the water immiscible organic phase from the aqueous phase; and crystallizing the purified compound from said water immiscible organic phase by the addition of an organic solvent.

2. The process of claim 1 wherein the alky, alkoxy and acyl groups contain up to 6 carbon atoms.

3. The process of claim 2 wherein Ar is a monosubstituted phenyl group and Z is —CH₂—CH₂—.

4. The process of claim 1 wherein heteroaryl is thienyl, furyl, thiazolyl, pyridyl or quinolinyl.

5. The process of claim 2 wherein Ar is a trifluoromethylphenyl.

6. The process of claim 2 wherein Ar is a trifluoromethylphenyl and Z is —C₂CH₂—.

7. The process of claim 1 wherein said compound is diethyl, 1,4-dihydro-2,6-dimethyl-1-[2-(4-morpholinyl)ethyl]-4-[2-(trifluoromethyl)phenyl-3,5-pyridinedicarboxylate.

8. The process of claim 1 wherein said organic solvent for dissolution of said compound is ethyl acetate or toluene.

9. The process of claim 1 wherein said acid in said organic solvent is an organic acid.

10. The process of claim 9 wherein said organic acid is p-toluenesulfonic acid or maleic acid.

11. The process of claim 1 wherein said organic solvent for the precipitation of the pure compound is heptane, n-hexane, or hexanes.

12. A process for the purification of a compound of the formula

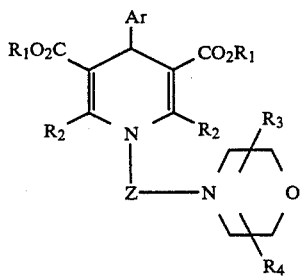

containing the residual starting material of the formula therein

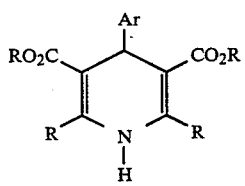

wherein Ar is heteroaryl, cycloalkyl having from 3 to 7 carbon atoms, naphthyl, indanyl, indenyl, tetrahydronaphthyl, or a radical of the formula

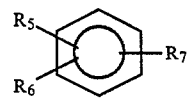

wherein each of $R_5$, $R_6$ and $R_7$ is independently H, alkyl, aryl, halo, lower alkoxy, nitro, amino, alkylmercapto, cyano, carboxy, carbalkoxy, sulfamyl, trifluoromethyl, hydroxy, acyloxy, methanesulfonyl, alkylamino or acylamino, and $R_5$ and $R_6$ when taken together, form a methylenedioxy; Z is alkylene containing 1 to about 5 carbon atoms in the principal chain; each $R_1$ is independently hydrogen, alkyl or alkoxyalkyl, with the proviso that only one $R_1$ may be hydrogen; $R_2$ is lower alkyl and $R_3$ and $R_4$ are independently hydrogen or alkyl; wherein the alkyl, alkoxy, and acyl groups contain up to 10 carbon atoms, comprising the steps of:

(a) dissolving said compound to be purified in an organic solvent to obtain a solution of 1 to 50% w/v;

(b) dissolving an organic acid in an organic solvent to obtain an acid solution of 1 to 50% w/v;

(c) adding said acid solution to said solution of the compound to be purified to precipitate the acid addition salt of said compound;

(d) collecting said precipitate;

(e) dissolving said precipitate in a two-phase solvent system, one of said two phases being a 1 to 50% w/v aqueous alkaline phase, the other of said two phases being a water immiscible organic phase;

(f) separating said water immiscible phase from said aqueous alkaline phase;

(g) crystallizing said compound by diluting said water immiscible organic phase with an organic solvent.

13. The process of claim 12 wherein said organic solvent to obtain dissolution of said compound therein is ethyl acetate or toluene.

14. The process of claim 12 wherein said organic acid is p-toluenesulfonic acid or maleic acid.

15. The process of claim 12 wherein the ratio of said aqueous alkaline phase to the water immiscible organic phase is 1:5 to 10:1.

16. The process of claim 12 wherein said organic solvent to crystallize said compound is selected from the group consisting of heptane, n-hexane or hexanes.

17. The process of claim 12 wherein the ratio of said water immiscible organic phase to said organic solvent is 3:1 to 1:10.

18. The process of claim 12 wherein the alkyl, alkoxy and acyl groups contain up to 6 carbon atoms.

19. The process of claim 18 wherein Ar is a monosubstituted phenyl group and Z is —CH₂—CH₂—.

20. The process of claim 12 wherein heteroaryl is thienyl, furyl, thiazolyl, pyridyl or quinolinyl.

21. The process of claim 18 wherein Ar is a trifluoromethylphenyl.

22. The process of claim 18 wherein Ar is a trifluoromethylphenyl and Z is —CH₂—CH₂—.

23. The process of claim 12 wherein said compound is diethyl 1,4-dihydro-2,6-dimethyl-1[2-(4-morpholinyl)ethyl]-4-[2-(trifluoromethyl)phenyl]-3,5-pyridinedicarboxylate.

* * * * *